(12) United States Patent
Canary et al.

(10) Patent No.: US 7,491,544 B2
(45) Date of Patent: Feb. 17, 2009

(54) CHIRAL PIPERIDINE AND QUINUCLEDINE LIGANDS

(75) Inventors: James Canary, New York, NY (US); Zhaohua Dai, Brooklyn, NY (US)

(73) Assignee: New York University, New York, NY (US)

( * ) Notice: Subject to any disclaimer, the term of this patent is extended or adjusted under 35 U.S.C. 154(b) by 506 days.

(21) Appl. No.: 10/441,262

(22) Filed: May 20, 2003

(65) Prior Publication Data

US 2004/0110304 A1   Jun. 10, 2004

Related U.S. Application Data

(60) Provisional application No. 60/381,335, filed on May 20, 2002, provisional application No. 60/408,880, filed on Sep. 9, 2002.

(51) Int. Cl.
*G01N 33/20* (2006.01)
*G01N 21/76* (2006.01)
*G01N 33/53* (2006.01)
*G01N 21/64* (2006.01)
*G01N 21/66* (2006.01)

(52) U.S. Cl. .................. 436/81; 436/172; 436/800; 422/82.07; 422/82.08

(58) Field of Classification Search .............. 436/81, 436/172, 800; 422/82.07, 82.08
See application file for complete search history.

(56) References Cited

U.S. PATENT DOCUMENTS 6,967,251 B2 * 11/2005 Haugland et al. ........... 544/289

\* cited by examiner

*Primary Examiner*—Jill Warden
*Assistant Examiner*—Keri A Moss
(74) *Attorney, Agent, or Firm*—Browdy and Neimark, P.L.L.C.

(57) ABSTRACT

Zn(II) is selectively detected in a sample by contacting the sample with a tripodal ligand with a piperidine or quinuclidine scaffold, one of which acts as a zinc sensor, in which the rigidity of the ligand scaffold is increased. The rigidity of the ligand scaffold can be increased by adding aromatic groups or cyclic hydrocarbon groups. Examples of aromatic groups include naphthalene and the like. Examples of cyclic groups include nitrogen-substituted cyclohexane and cyclohexene such as piperidine.

8 Claims, 7 Drawing Sheets

6    7

8    9

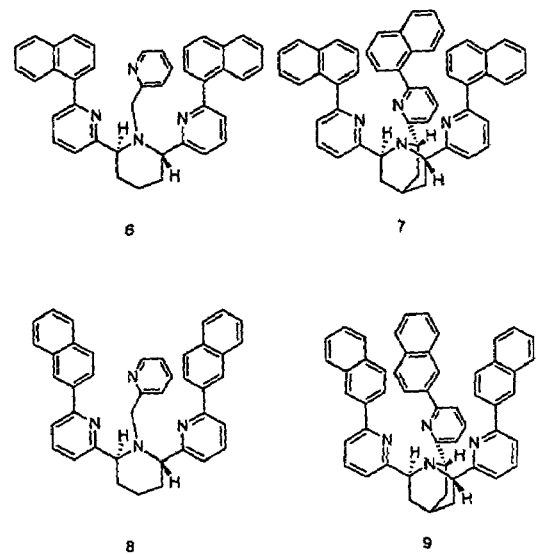
Figure 4.
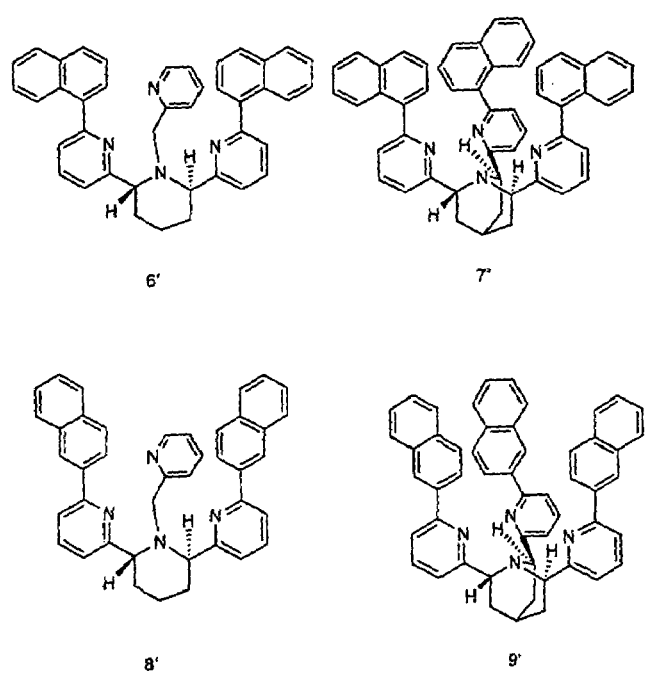
Figure 5. Mirror images of the compounds shown in Fig. 4.

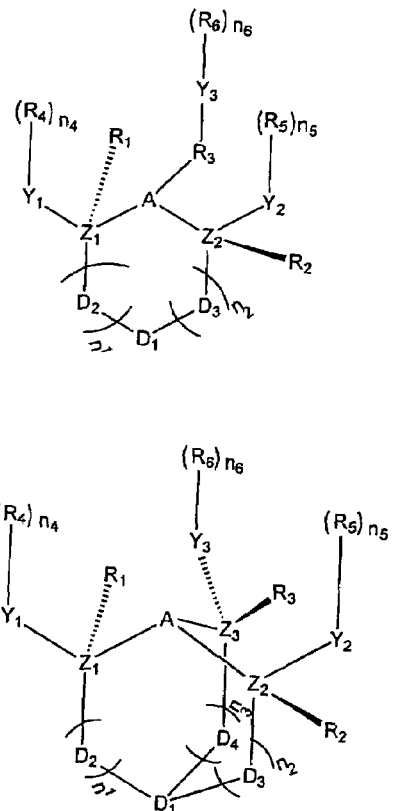
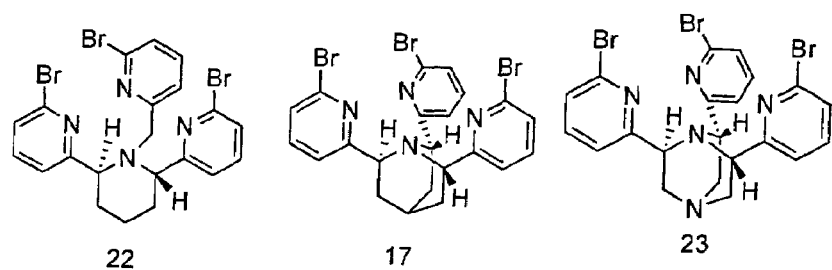
Figure 6.
Figure 7. Key intermediates involved in the syntheses.

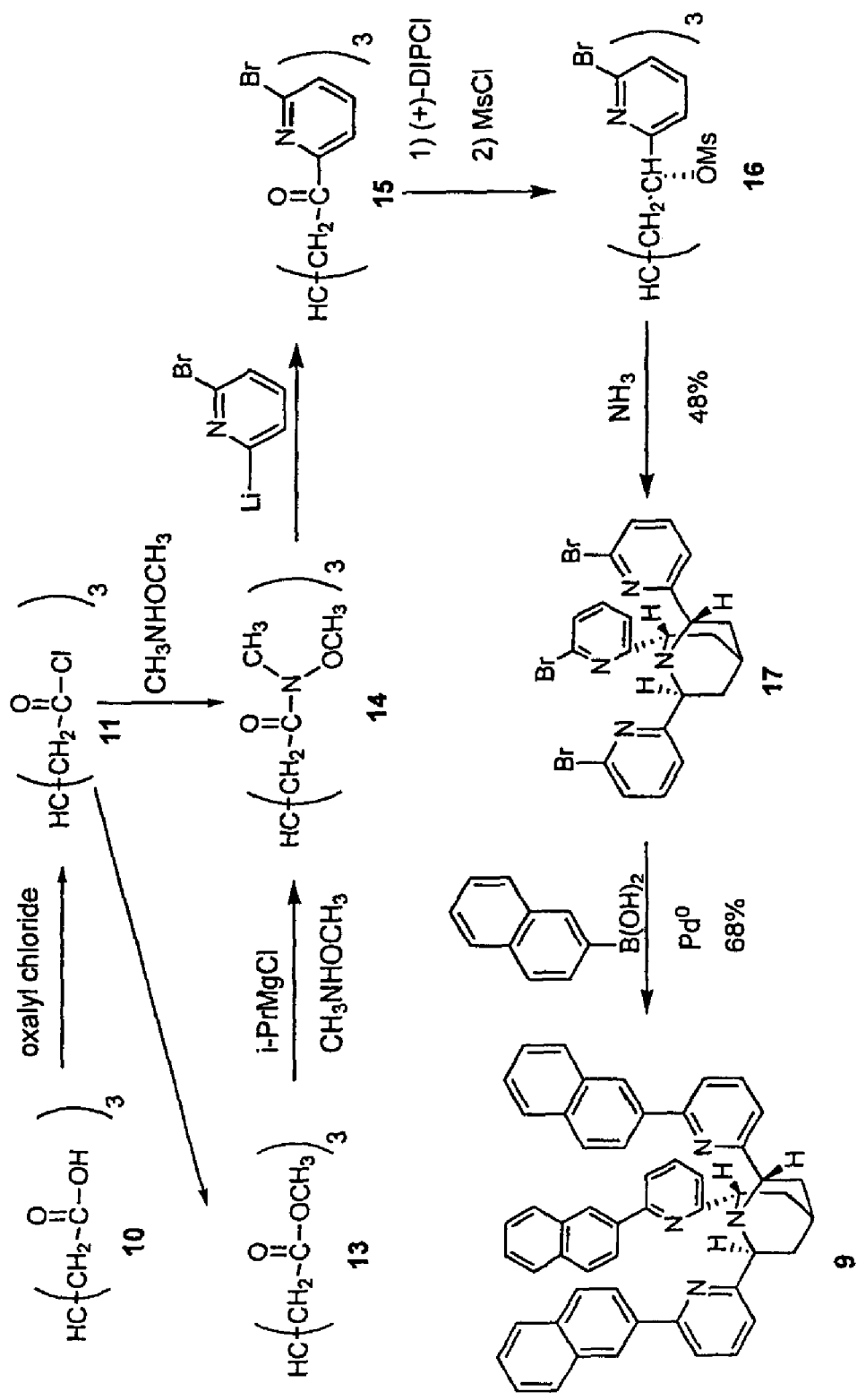
Figure 8. Typical synthesis of a quinuclidine compound.

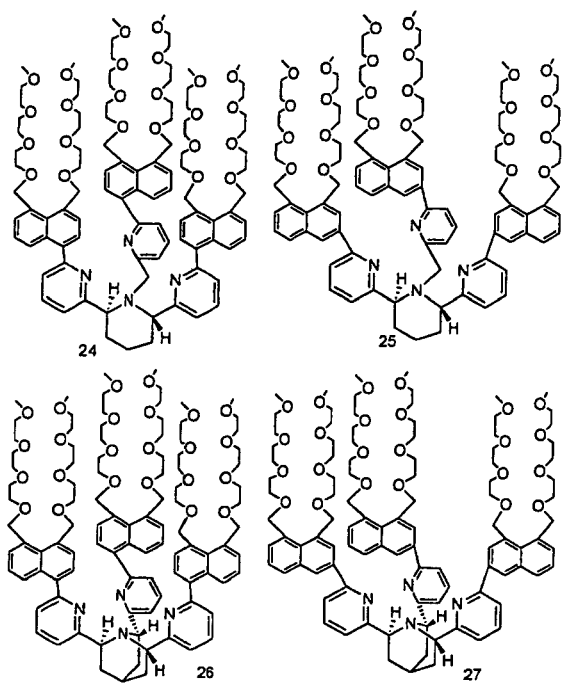
Figure 9. Compounds with solubilizing triethylene glycol groups attached.
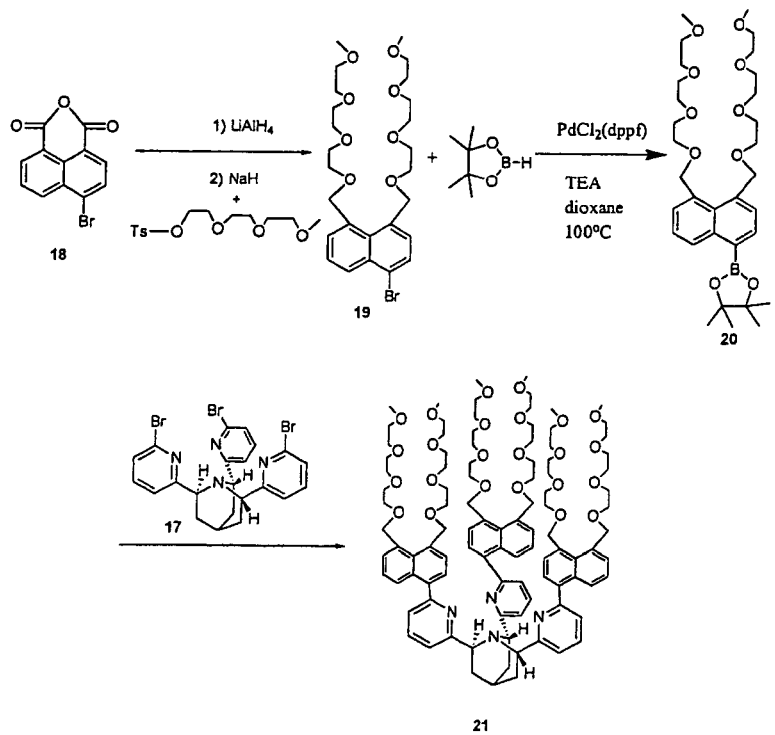
Figure 10. Synthesis of a solubilized quinuclidine compound.

CHIRAL PIPERIDINE AND QUINUCLEDINE LIGANDS

GOVERNMENT INTEREST

This invention was supported by NIH Grant No. GM49170 and NSF Grant No. CHE0079072.

CROSS-REFERENCE TO RELATED APPLICATIONS

The present application is a non-provisional of Ser. No. 60/381,335, filed May 20, 2002, and Ser. No. 60/408,880, filed Sep. 9, 2002, the entire contents of which are hereby incorporated by reference.

FIELD OF THE INVENTION

The present invention relates to controlling the selectivity toward zinc ion over copper (II) of ligands which have a central piperidine or quinuclidine scaffold, as well as to compounds which are useful as catalysts for asymmetric catalysis.

BACKGROUND OF THE INVENTION

Zinc is an important element in most cells, and variation from normal concentration is associated with many diseases, such as Alzheimer's syndrome (Cualungee et al., 1999; Suh et al., 2000; Xuang et al., 2000; Andrasi et al., 2000). Rapid analysis of trace metal cations requires both high sensitivity and selectivity. Fluorescent chemosensors, which consist of a recognition moiety and a signaling moiety, are particularly attractive because they are inherently highly sensitive.

One problem with the sensitivity of fluorescent chemosensors is that other metal ions may interfere. Many reported fluorescent chemosensors for Zn(II) suffer from interference from binding Cu(II), which commonly forms more stable complexes that Zn(II) with many ligands (Walkup et al., 1997; Hirano et al., 2000; Fahrnti et al., 1999).

In a previous study (Castagnetto et al., 1998), it was found the recognition of Zn(II) by compound I, shown in FIG. 1, benefited from both fluorescence enhancement as well as chiroptical signal increase. However, Cu(II) was a significant competitor for Zn(II) in that system, as it has been found to be in many published systems.

In the pharmaceutical industry, asymmetric synthesis is crucial. Chiral coordination complexes are frequently used in asymmetric synthesis and chiral discrimination technologies. Among known chiral ligands, $C_2$-symmetric compounds have been widely and successfully used in enantioselective reactions. It has been suggested that a higher symmetry would give better control of enantioselectivity. While numerous classes of achiral $C_3$-symmetric ligands exist, there are relatively few examples of chiral $C_3$-symmetric ligands.

SUMMARY OF THE INVENTION

It is an object of the present invention to overcome the aforesaid deficiencies of the prior art.

It is another object of the present invention to provide increased selectivity for Zn(II) over Cu(II) in ligand stereochemistry.

It is a further object of the present invention to provide chiral $C_3$-symmetric ligands.

It is another object of the present invention to provide trans-piperidine or all-trans-quinuclidine central scaffold structure compounds.

It is yet another object of the present invention to provide compounds that can be used in asymmetric catalysis.

The following compounds in enantiopure form are shown in the compounds of FIG. 4. The compounds of the present invention can be used as a Zn(II) ion sensor with improved Zn(II)/Cu(II) selectivity. Additionally, the compounds of the present invention can be used as asymmetric catalysts, e.g., for asymmetric Michael reactions. For this purpose, the uniqueness is in the type of reaction that is accomplished, and the substrate profile that works well with this catalyst.

The rigidity of the ligand scaffold can be increased by adding aromatic groups or cyclic hydrocarbon groups. Examples of aromatic groups include naphthalene and the like. Examples of cyclic groups include nitrogen-substituted cyclohexane and cyclohexene such as piperidine.

The rigidity of the ligand scaffold was increased by synthesizing piperidine analogues of compound 2, which might be expected to destabilize Cu(II) binding as compared to Zn(II). Copper(II) is a d9, metal, which means that the bonding in Cu(II) complexes is more covalent than in zinc, thus affording greater potential for differentiation due to ligand stereochemistry. Zn(II) is a d10 metal, and is less demanding than Cu(II). A similar rationale was used to design ligands that stabilized Cu(I) over Cu(II) (Ambundo et al., 1999).

FIG. 4 shows compounds 6 and 8 in enantiopure form.

Thus, the present invention provides a method for selectively detecting Zn(II) in a sample by contacting the sample with a tripodal ligand with a piperidine or quinuclidine scaffold, one of which acts as a zinc sensor, in which the rigidity of the ligand scaffold is increased. The compounds of the invention can also be used as catalysts for asymmetric technology.

BRIEF DESCRIPTION OF THE DRAWINGS

FIG. 4 shows compounds of the present invention in enantiopure form.

FIG. 5 shows mirror images of the compounds in FIG. 4.

FIG. 6 shows the generalized structure of compounds according to the present invention.

FIG. 7 shows key intermediates involved in the syntheses of compounds according to the present invention.

FIG. 8 illustrates a typical synthesis of a quinuclidine compound.

FIG. 9 shows quinuclidine compounds of the present invention with triethylene glycol groups attached.

FIG. 10 illustrates synthesis of a solubilized quinuclidine compound.

DETAILED DESCRIPTION OF THE INVENTION

Figure 1:
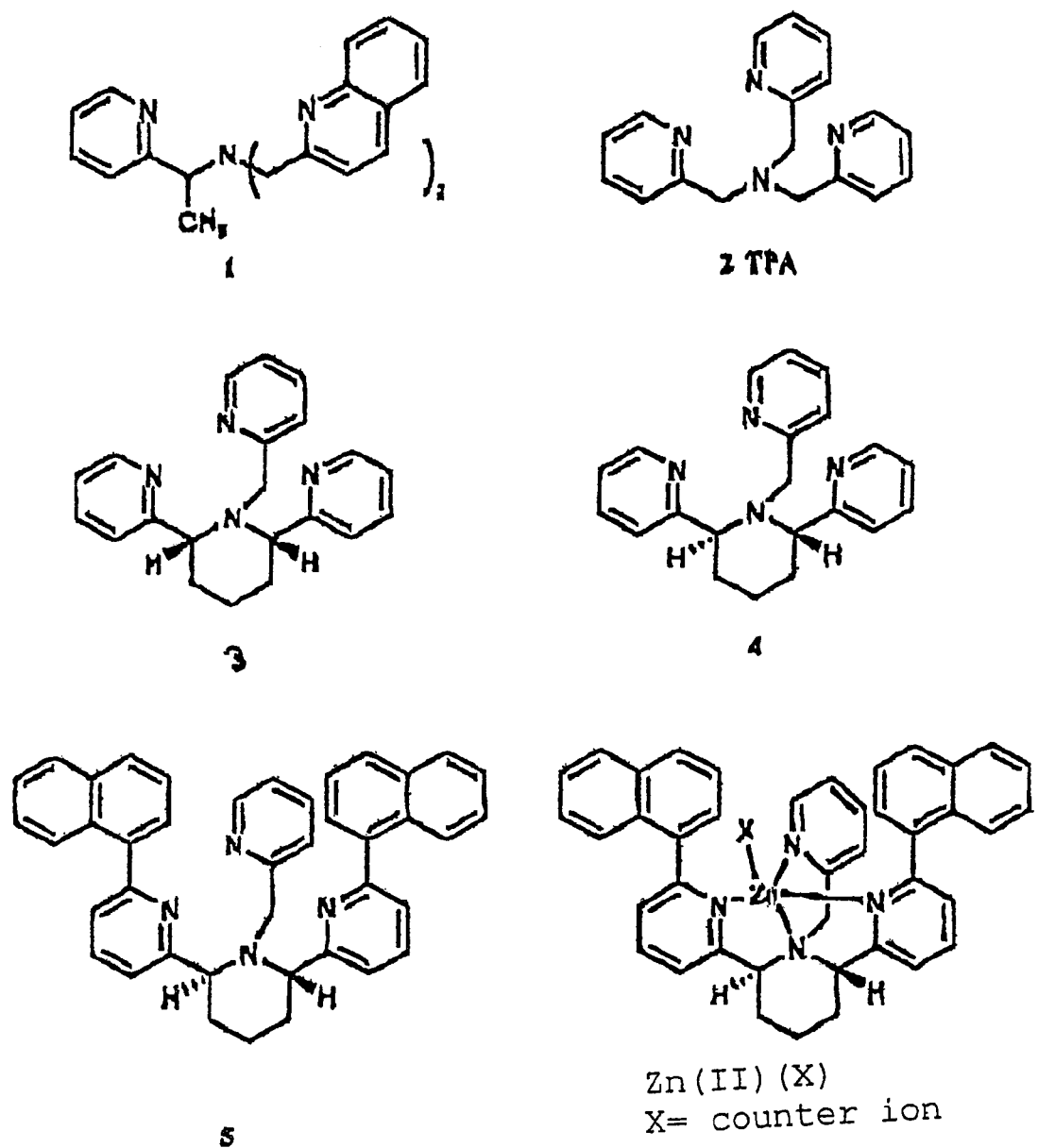
FIG. 1 illustrates fluorescent ligands for Zn(II).

Compounds 3 and 4 were prepared as described by X. Xu in a Ph.D. dissertation at New York University, 2000. The binding constants were determined by potentiometric titration as described in Martell et al., 1992. For the cis-piperidine derivative, compound 3, Cu(II) and Zn(II) gave log $\beta$=14.8 and 10.1, respectively. For the trans-ligand, compound 4, the numbers were found to be 12.0 and 11.2, respectively. The parent compound TPA, compound 2, shows log β=16.15, compared to 11.00 for Zn(II) (Anderegg et al., 1977). Thus, the ratios of the association constants for binding Cu(II) over Zn(II) of compounds 2, 3, and 4 are $1.4 \times 10^5$, $5 \times 10^4$, and 6, respectively. While the cis-ligand, compound 3, showed diminished binding for both Cu(II) and Zn(II), the trans-ligand, compound 4, showed even worse binding of Cu(II) but slightly stronger binding of Zn(II) over TPA.

The differences in stability were estimated using PM3/tm calculations of the heat of formation of the [M(L)Cl]+(M=Cu (II), Zn(II)) complexes. A small difference was obtained for the Zn(II) complexes of 181.87 and 183.6 kcal/mole for compounds 3 and 4, respectively. A larger difference was observed for the Cu(II) complexes, namely 106.8 and 112.6 kcal/mole. These calculations agree with the observation that the binding of Zn(II) is not much dependent on ligand stereochemistry, while for Cu(II), ligand 3 is significantly preferred. The computed structures showed greater similarity of the [Cu(TPA)Cl]+Cu—N bond lengths in the complex of 3 than in the complex of 4. Thus, trans-ligand compound 4 appears to distort the coordination sphere of the copper ion, resulting in a less stable complex.

As used herein, alkyl carbon chains, if not specified, contain from 1 to 20 carbon atoms, preferably from 1 to 16 carbon atoms, and are straight or branched. FIG. 6 shows the generalized structure of compounds according to the present invention. The compound can be a single ring, or a multiple ring compound such as two rings or three rings.

In the formula of FIG. 6,

A is an atom that can coordinate to a metal ion such as nitrogen, oxygen, or sulfur;

$D_1$ is the bottom pivotal atom. $D_1$ can be carbon, nitrogen, sulfur, phosphorus, etc;

$D_2$, $D_3$ and $D_4$ can be carbon, nitrogen, sulfur, phosphorus, etc., and can be the same or different. $D_2$, $D_3$ and $D_4$ can repeat themselves $n_1$, $n_2$ and $n_3$ times, wherein $n_1$, $n_2$ and $n_3$ can be the same or different. The ring size can vary;

$Z_1$, $Z_2$, $Z_3$ can be the same or different, and are chiral atoms such as carbon.

$R_1$, $R_2$, and $R_3$ can be the same or different and can be hydrogen, alkyl, substituted alkyl, aryl, or substituted aryl;

$Y_1$, $Y_2$ and $Y_3$ can be the same or different and contain an atoms that can coordinate to a metal ion. $Y_1$, $Y_2$ and $Y_3$ can optionally be chromophores which are capable of absorbing light. $Y_1$, $Y_2$ and $Y_3$ are selected from the group consisting of $C_1$-$C_{20}$ alkyl, substituted $C_1$-$C_{20}$ alkyl, aryl; having up to 20 carbon atoms, and substituted aryl; and $R_4$, $R_5$ and $R_6$ are selected from the group consisting of $C_1$-$C_{20}$ alkyl, substituted $C_1$-$C_{20}$ alkyl, aryl having up to 20 carbon atoms, substituted aryl, halide, hydroxyl, alkoxy, carboxyl acid groups, amino groups, and amide groups. They may optionally contain chromophores. $R_4$, $R_5$ and $R_6$ are optionally connected to form at least one other ring.

FIG. 7 illustrates key intermediates involved in synthesizing compounds of the present invention.

FIG. 8 illustrates a typical synthesis of a quinuclidine compound of the present invention. A tris-acid compound 10 was converted to a tris-acid chloride 11 by reacting it with an excess amount of oxalyl chloride in the presence of two drops of dry DMF. Then compound 11 was converted to the tris-ester 13, which was reacted with the Grignard reagent isopropylmagnesium chloride and N,O-diemethylhydroxyamine to yield tris-amide 14. The tris-amide 14 was also obtained by reacting compound 11 directly with N,O-dimethylhydroxyamine. Then compound 14 was reacted with 2-bromo-6-lithio-pyridine to form the tris-ketone 15, which was subsequently reduced by a chiral reductant DIP-chloride and then reacted with mesyl chloride to produce an activated chiral tris-alcohol in the form of tris-mesylate 16 having three chiral centers of the same configuration. Compound 16 was reacted with ammonia to afford the all-trans rigid scaffold 17. Reacting 17 with 2-naphthyl boronic acid in a Suzuki coupling resulted in target compound 9.

The compounds of the present invention can be made soluble in water by attaching triethylene glycol groups, as shown in FIG. 9.

FIG. 10 illustrates synthesis of a solubilized quinuclidine compound according to the present invention. In this synthesis, 4-bromo-1,8-naphthalic anhydride 18 was reduced with lithium aluminum hydride to form a dialcohol. This dialcohol was subjected to sodium hydride and tosylated tri(ethyleneglycol)monomethyl ether in dry DMF to yield compound 19. Reacting compound 19 with pinacolborane resulted in the expected pinacolboronate 20. Compound 20 was coupled with the rigid scaffold 17 in a Suzuki coupling to give the desired water-soluble compound 21.

As used herein an alkyl group substituent includes halo, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl rings.

The term "aryl" herein refers to aromatic cyclic compounds having up to 20 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused ring systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

More rings which may be joined together in a fused, bridged, or spiro-connected fashion, and may be optionally substituted with one or more alkyl group substituents, for example, pyrrolidinyl, piperidinyl, alkylpiperidinyl, or morpholinyl.

Figure 2:
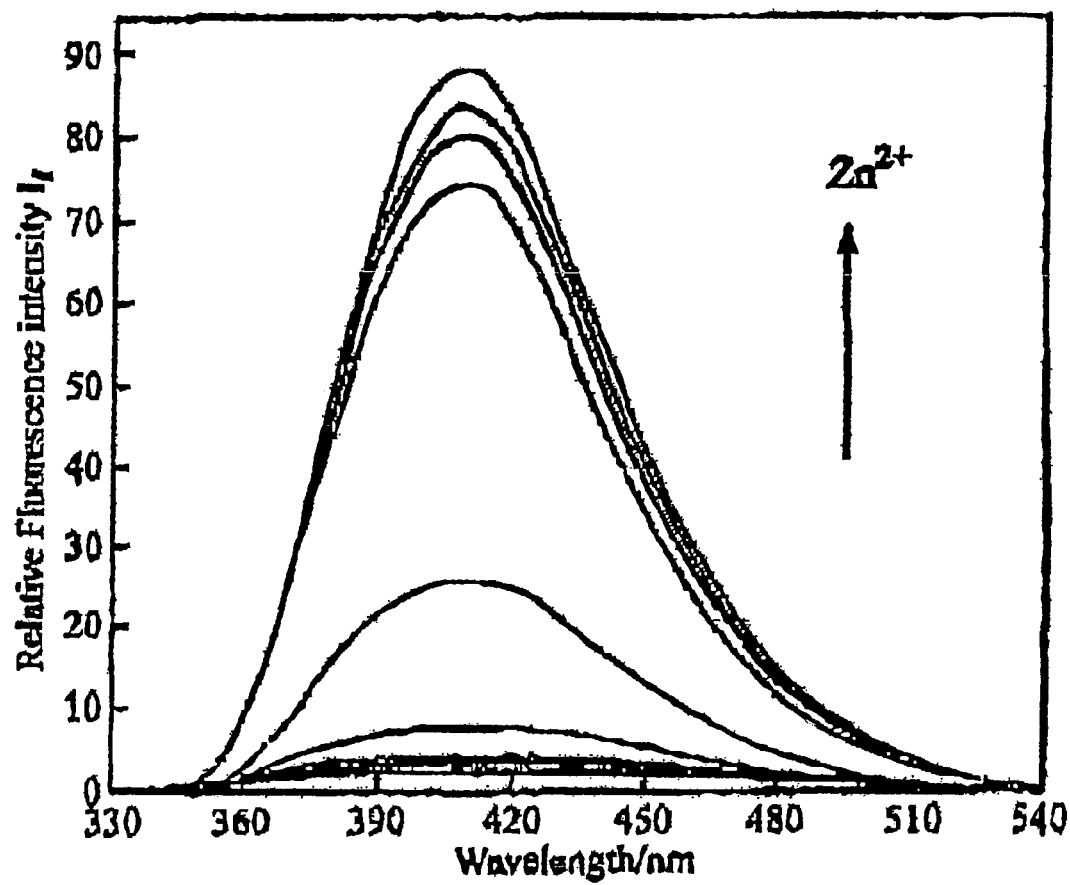
FIG. 2 shows the fluorescence response of compound 5 (1 µM) to buffered $Zn^{2+}$ inclusions. Spectra were acquired in 1% methanol aqueous solution (0.1 M KNO3, 50 mM HEPES, pH 7, 25° c.) with excitation at 300 nm. The zinc ion concentration was buffered by 10 mM EGTA with total zinc concentration ranging from 0 to 9 mM. The spectra shown are for total $An^{2+}$ at 0. 0.2, 0.4, 3, 4, 5, 6, 7, and 9 mM with corresponding free $Zn^{2+}$ at 0, 10-10.29, 10-9.98, 10-8.78, 10-8.60, 10-8.42, 10-8.23, 10-7.65M, respectively.

Compound 5 was prepared to examine whether these stereochemical observations could be used to produce a fluorescent chemosensor (Xu, 2000). This compound contains the metal binding domain of trans-ligand compound 4 with a signaling domain consisting of two naphthalene moieties. This system works similar to other photoinduced electron transfer (PET) chemosensors in that the fluorescence of the naphthalene moieties is diminished in the absence of metal ion, but increases nearly 20-fold upon binding Zn(II), as shown in FIG. 2. In the free ligand, when the fluorophore is excited, a PET process can take place. The electron can transfer from the piperidine nitrogen atom to the fluorophore, thereby quenching the fluorescence. Upon binding Zn(II), the oxidation potential of the amino-N-atom increases significantly, so that PET is checked and the fluorophore exhibits strong fluorescence. A job plot of the fluorescence indicated stoichiometric binding, which was expected because of the similarity to other Zn(II) complexes (Allen et al., 1995; Canary et al., 1998). The 1:1 log β of compound 5 for Zn(II) was found to be 9.3.

Figure 3:
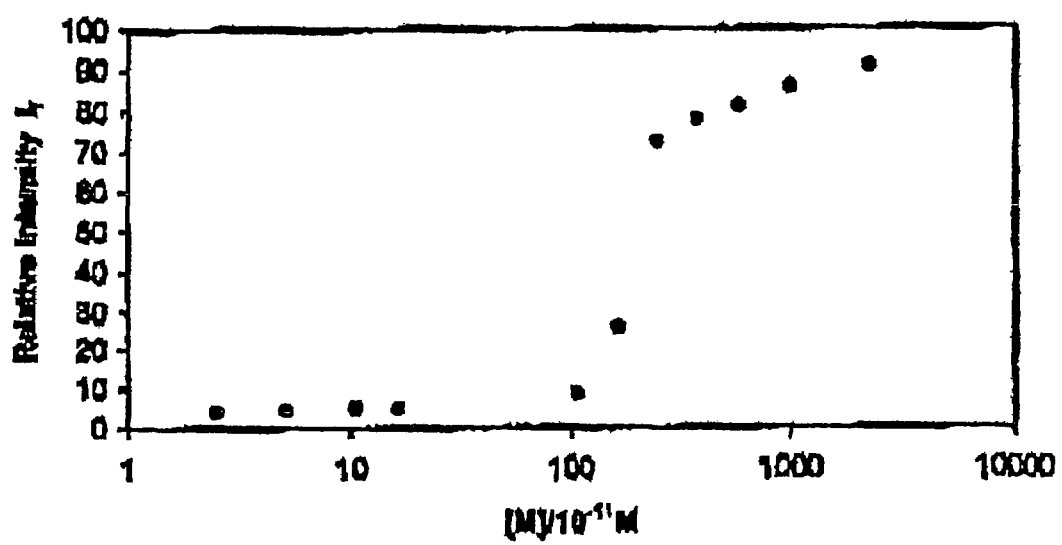
FIG. 3 shows the relative fluorescence intensity of compound 5 with different amounts of $Zn^{2+}$ at 405 nm. The conditions are the same as those of FIG. 2. The points shown are for total $Zn^{2+}$ at 0, 0.2, 0.4, 0.6, 3, 4, 5, 6, 7, 8, and 9 mM, respectively.

The sensitivity of compound 5 for Zn(II) was found to be nanomolar. A plot of the measured fluorescence intensity at 405 nm (near λ max) against free Zn(II) resulted in a sigmoidal curve, as shown in FIG. 3. This experiment used EGTA to control the free Zn(II) concentration. For these data, the lower detection limit of compound 5 toward Zn(II) is 1 nM and saturation is reached above about 100 nM, suggesting that compound 5 is optimal. For detecting Zn(II) concentrations in the nanomolar range in aqueous fluids.

The issue of selectivity was assessed. It was found that biologically relevant metal ions have little or no influence on the sensing properties of compound 5. The ions sodium (1.0 M), potassium (0.1 M), magnesium (1 mM), or calcium (1 mM) do not significantly change the fluorescence of compound 5 or a complex of compound 5 with Zn(II) at micromolar concentrations. As expected, based on the studies of compounds 3 and 4, Cu(II) did compete with Zn(II) for compound 5, resulting in the quenching of fluorescence energy transfer between the paramagnetic metal ion and the fluorophores. A competition experiment involving titrating Zn(II) and Cu(II) gave log β for Cu(II)=10.6. Thus, the improved selectivity that had been found for the ligand compound 4 was also observed with compound 5.

It was found that increasing the ligand rigidity was able to improve the selectivity of Zn(II) over Cu(II) for compound 4 and 5 vs. compound 2 by a factor of 104. Thus, rigidification of the receptor yields improved selectivity for Zn(II) over Cu(II).

The sensitivity of compound 5 for Zn(II) was found to be nanomolar. A plot of the measured fluorescence intensity at 405 nm (near λ max) against free Zn(II) resulted in a sigmoidal curve, as shown in FIG. 3. This experiment used EGTA to control the free Zn(II) concentration. Of these data, the lower detection limit of compound 5 toward Zn(II) is 1 nM and saturation is reached above about 100 nM, suggesting that compound 5 is optimal for detecting Zn(II) concentrations in the nanomolar range in aqueous fluids.

The issue of selectivity was assessed. It was found that biologically relevant metal ions have little or no influence on the sensing properties of compound 5. The ions sodium (1.0 M), potassium (0.1 M), magnesium (1 mM), or calcium (1 mM) do not significantly change the fluorescence of compound 5 or a complex of compound 5 with Zn(II) at micromolar concentrations. As expected, based on the studies of compounds 3 and 4, Cu(II) did compete with Zn(II) for compound 5, resulting in the quenching of fluorescence energy transfer between the paramagnetic metal ion and the fluorophores. A competition experiment involving titrating Zn(II) and Cu(II) gave log β for Cu(II)=10.6. Thus, the improved selectivity that had been found for the ligand compound 4 was also observed with compound 5.

It was found that increasing the-ligand rigidity made it possible to improve the selectivity of Zn(II) over Cu(II) for compounds 4 and 5 vs. compound 2 by a factor of 10,000. Thus, rigidification of the receptor yields improved selectivity for Zn(II) over Cu(II).

Compounds 6, 7, 8, and 9 can be substituted at any position with any aryl or alkyl substituents. Atom D1, can be replaced by atoms other than carbon, such as nitrogen.

The compounds of the present invention can also be used for asymmetric synthesis of organic compounds, such as beta-amino acids, ketones, and the like.

All references cited herein are hereby incorporated by reference.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In a method of detecting Zn(II) in a sample in the presence of interfering ions by fluorescent sensing, comprising combining the sample with a chemosensor that binds preferentially to Zn(II) in the presence of Cu(II) ions and subjecting the sample to light of a wavelength of from 350 nm to 540 nm wherein a compound having the following formula is used as a fluorescent chemosensor:

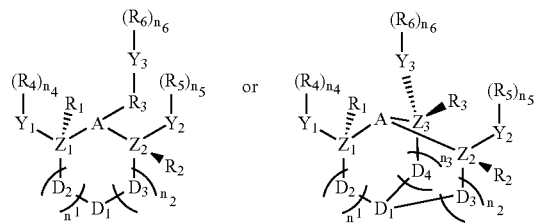

wherein

A is nitrogen;

$D_1$ is carbon or nitrogen;

$D_2$, $D_3$ and $D_4$ are carbon or nitrogen and can be the same or different;

$Z_1$, $Z_2$, $Z_3$ are the same or different, and are chiral atoms;

$R_1$, $R_2$, and $R_3$ are the same or different and are hydrogen, alkyl, substituted alkyl, aryl, heteroaryl or substituted aryl and if $R_3$ is H, then $Y_3$ and $R_6$ are not present;

$Y_1$, $Y_2$ and Y3 are the same or different and are selected from the group consisting of (a) moieties that contain an atom that coordinates to Zn(II) and (b) chromophores capable of absorbing light, wherein at least one of $Y_1$, $Y_2$ and $Y_3$ binds to zinc;

wherein the moieties capable of binding to Zn(II) are selected from the group consisting of $C_1$-$C_{20}$ alkyl, substituted $C_1$-$C_{20}$ alkyl, aryl having up to 20 carbon atoms, heteroaryl and aryl;

$R_4$, $R_5$ and $R_6$ are selected from the group consisting of $C_1$-$C_{20}$ alkyl, substituted $C_1$-$C_{20}$ alkyl, aryl having up to 20 carbon atoms, substituted aryl, halide, hydroxyl, alkoxy, carboxyl acid groups, amino groups, and amide groups;

$R_4$, $R_5$ and $R_6$ are optionally connected to form at least one other ring; and detecting fluorescence when the fluorescent chemosensor binds to Zn (II).

2. The method according to claim 1 wherein the fluorescent chemosensor is selected from the group consisting of:

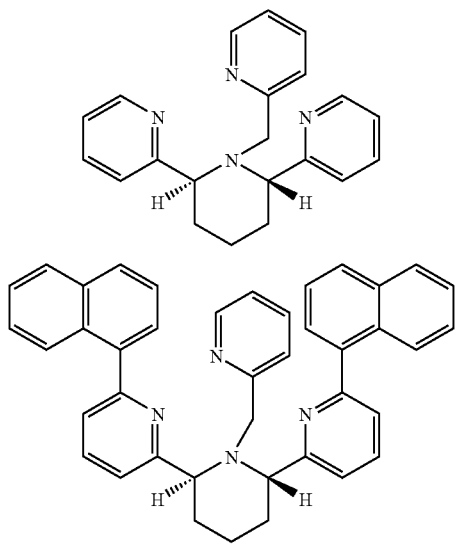

3. The method according to claim 1 wherein the fluorescent chemosensor includes a trans-ligand.

4. The method according to claim 1 wherein the compounds are made water soluble by attaching thereto a triethyleneglycol group.

5. The method according to claim 1, wherein the fluorescent chemosensor is

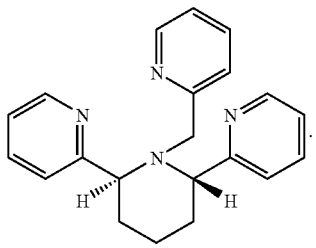

6. The method according to claim 1, wherein the fluorescent chemosensor is

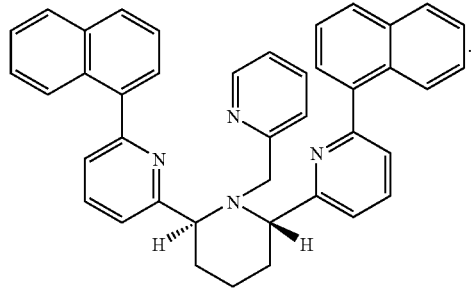

7. A method of detecting Zn (II.) in a sample in the presence of interfering ions comprising adding a chemosensor to the sample and subjecting the sample to light of a wavelength of from 350 nm to 540 nm wherein a compound selected from the group consisting of

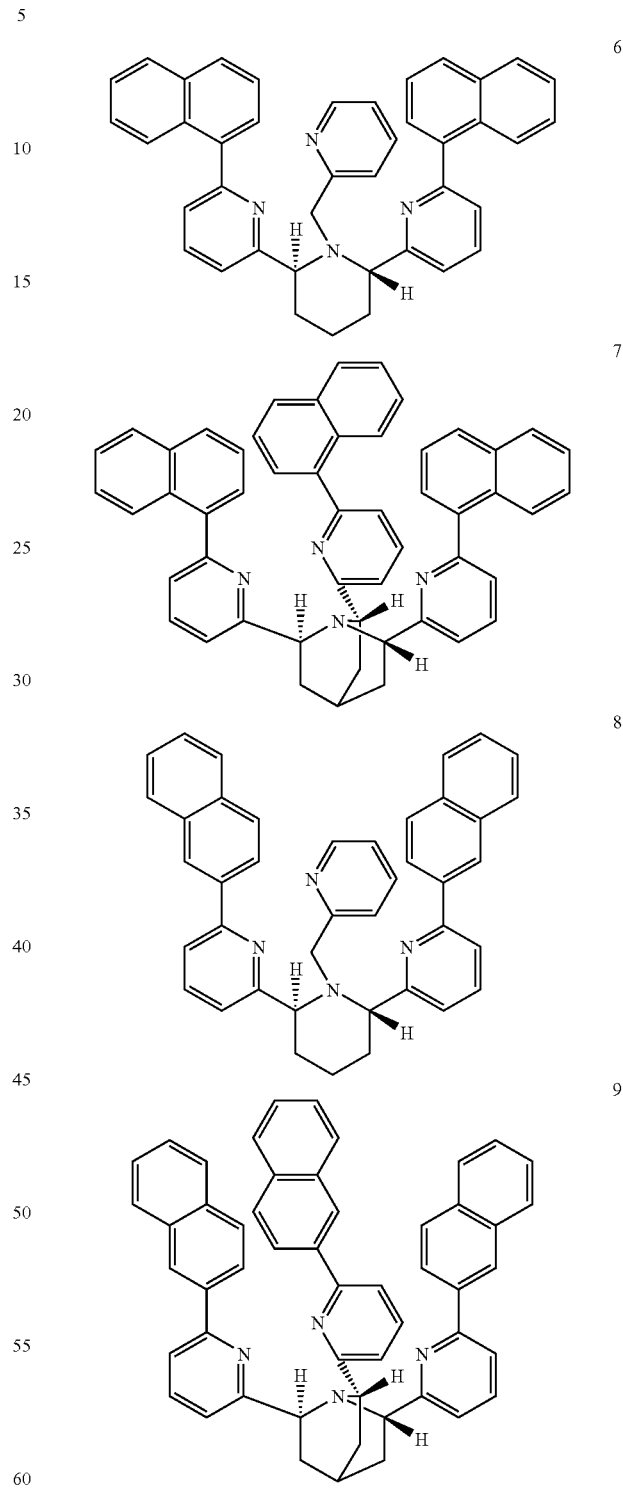

that preferentially binds to Zn(II) is used as a fluorescent chemosensor and detecting fluorescence produced when the sample contains Zn (II).

8. The method according to claim 4 wherein the compounds have the following formula:

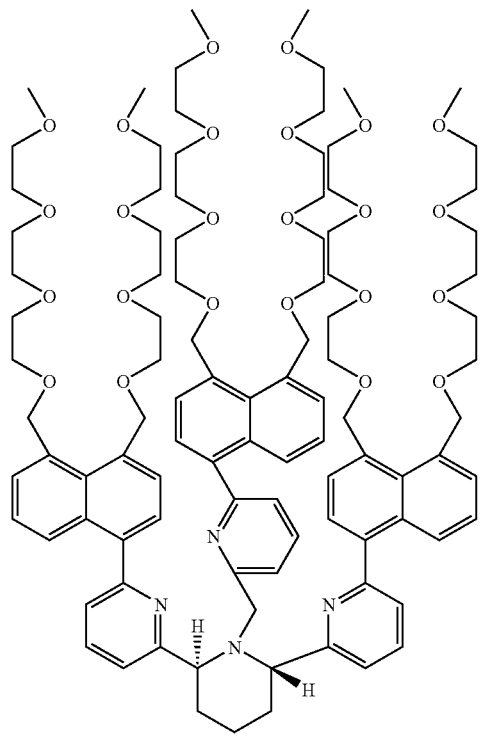
24
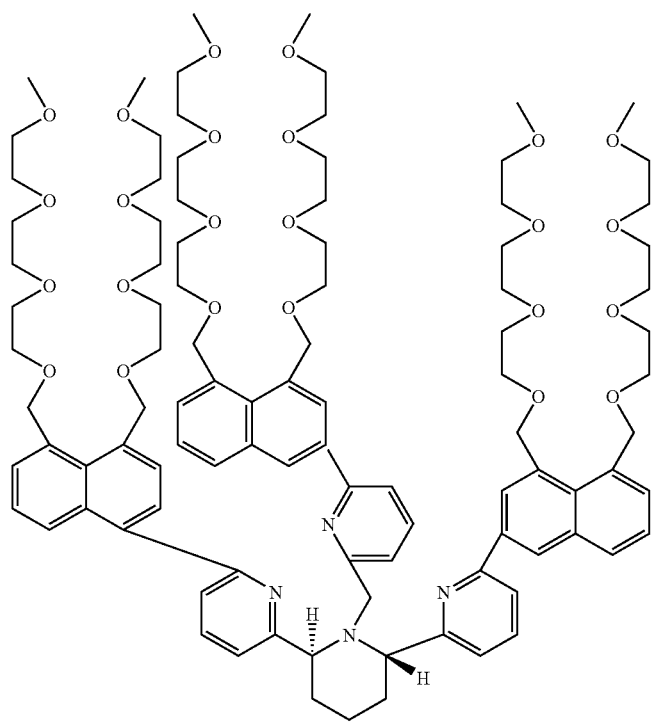
25

26
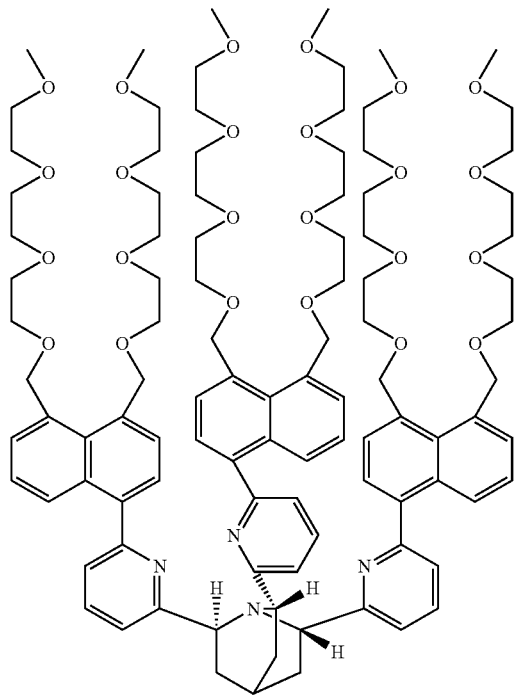
27
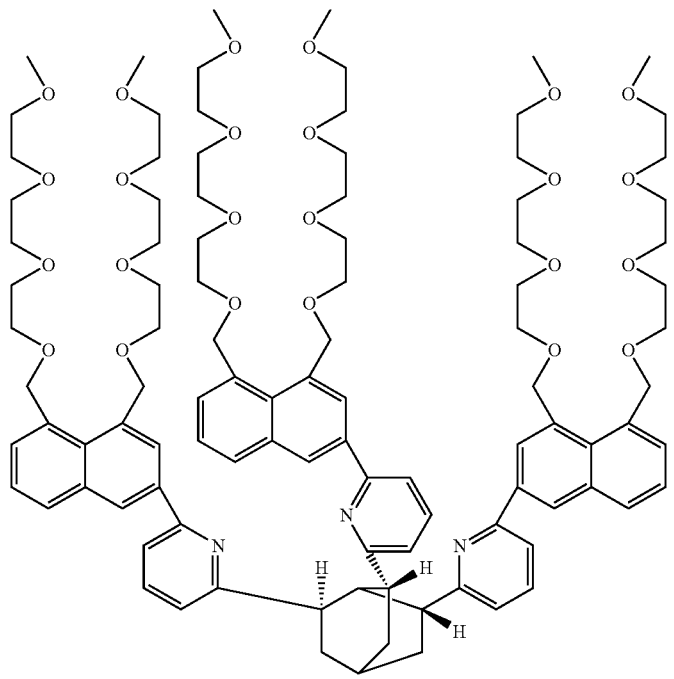
* * * * *